United States Patent [19]

Kjelleberg et al.

[11] Patent Number: 4,859,656

[45] Date of Patent: Aug. 22, 1989

[54] METHOD OF DETACHING MICRO-FLORA AND COMPOSITIONS THEREFOR

[75] Inventors: Staffan Kjelleberg, Göteborg; Peter Rönnow, Mölnlycke, both of Sweden

[73] Assignee: Chemical Dynamics Sweden AB, Skara, Sweden

[21] Appl. No.: 908,019

[22] PCT Filed: Dec. 10, 1985

[86] PCT No.: PCT/SE85/00515

§ 371 Date: Sep. 10, 1986

§ 102(e) Date: Sep. 10, 1986

[87] PCT Pub. No.: WO86/03937

PCT Pub. Date: Jul. 17, 1986

[30] Foreign Application Priority Data

Jan. 10, 1985 [SE] Sweden ................................ 8500102

[51] Int. Cl.⁴ ................... A61K 31/715; A61K 6/00; A61K 31/725; A61K 33/06
[52] U.S. Cl. ........................................ 514/54; 514/57; 514/60; 514/835; 424/49; 523/105
[58] Field of Search ............... 514/60, 835, 54, 57; 424/49; 523/105

[56] References Cited

U.S. PATENT DOCUMENTS

| | | | |
|---|---|---|---|
| 4,282,204 | 8/1981 | Phillips et al. | 424/49 |
| 4,327,079 | 4/1982 | Aoki | 424/49 |
| 4,360,513 | 11/1982 | Buck | 514/835 |
| 4,537,767 | 8/1985 | Rothman et al. | 514/60 |
| 4,619,825 | 10/1986 | Eigen et al. | 424/49 |
| 4,704,360 | 11/1987 | Shoham et al. | 435/99 |

FOREIGN PATENT DOCUMENTS

0962598 2/1975 Canada.
0980255 12/1975 Canada.
0048616 3/1982 European Pat. Off..

*Primary Examiner*—Ronald W. Griffin
*Assistant Examiner*—Nancy S. Carson
*Attorney, Agent, or Firm*—Dennison, Meserole, Pollack & Scheiner

[57] ABSTRACT

The invention relates to a method of controlling microorganisms adhered to surfaces in biological material, by administering substances which alter the water-structure binding capacity of surfaces and phase-boundaries.

To remove micro-organisms from the surfaces, organic and inorganic salts are used in combination with organic polymers, preferably biopolymers, with positively and/or negatively charged groups such as amino groups and carboxyl groups.

The invention also relates to compositions and preparations for performing the method, e.g. ointments, pastes and washing liquids containing the above-mentioned substances, as well as toothpaste containing one or more organic or inorganic salts together with the above-mentioned polymers.

15 Claims, 4 Drawing Sheets

METHOD OF DETACHING MICRO-FLORA AND COMPOSITIONS THEREFOR

The present invention relates to a method of greatly increasing the detachment of micro-flora adhered to various types of boundary surfaces/inter-phases by the addition of various combinations of polymers, preferably biopolymers, to treatment solutions. The invention also relates to preparations for achieving the above-mentioned result.

In our earlier patent application (Pat. app. No. 8206250-6) we were able to establish that bacteria irreversibly adhered to various boundary surfaces can be made to detach themselves to a greater or lesser extent simply due to the action of concentrated salt solutions.

This is illustrated by, but not limited to the following experiments in a model system.

A number of glass tubes, all the same size, were immersed in a suspension of bacteria marked with a radioactive isotope (tritium) and the bacteria were allowed to adhere over a period of 30 minutes. The glass tubes were then removed one by one and rinsed by repeated dipping (30 times) in a buffer solution in order to remove reversibly bound bacteria. Only the irreversibly bound bacteria then remained on the glass tube. The glass tube was then immersed in a salt solution for 5 minutes. After rinsing, the quantity of bacteria adhered to the tube was determined by measuring the radiation in a liquid scintillator.

A comparison of the various glass tubes which had been immersed in salt solution of various concentrations, with control tubes which had undergone the same treatment with the exception of immersion in the salt solution, enabled assessment of the effect of the salt solution on the irreversibly bound bacteria. The table below and the accompanying figures show the effects of the various salts on detachment of the irreversibly adhered bacteria, expressed as a percentage of the quantity of irreversibly adhered bacteria before the salt treatment. The concentrations of the solutions are in multiples of a specific critical concentration (C) of the basic solution.

Of the salts tested in this series of experiments, magnesium sulphate ($MgSO_4$) gave the strongest detaching effect. However, magnesium chloride ($MgCl_2$) and ammonium acetate ($NH_4Ac$) solutions also gave good results, whereas ammonium sulphate (($NH_4)_2SO_4$) solutions gave a slightly different pattern.

Several other compounds and salts have been tested besides those mentioned in this series of experiments, and the results were similar.

TABLE

Detachment percentage of irreversibly adhered bacteria after treatment.

The number of bacteria irreversibly adhered to the glass tube was $3.0 \times 10^6$ before treatment.

Salt concentration in multiples of basic solution C

| Salts | 0.05 × C | 0.1 × C | 0.2 × C | 0.5 × C |
| --- | --- | --- | --- | --- |
| $MgSO_4$ | 41 | 54 | 28 | 28 |
| $MgCl_2$ | 20 | 40 | 21 | 25 |
| $NH_4$Acetate | 8.5 | 41 | 17 | 24 |
| $(NH_4)_2SO_4$ | 31 | 36 | 44 | 28 |

The detachment of microorganisms as a result of exposure to solutions of salts and/or polymers can be seen in the attached drawings, in which.

Figure 1:
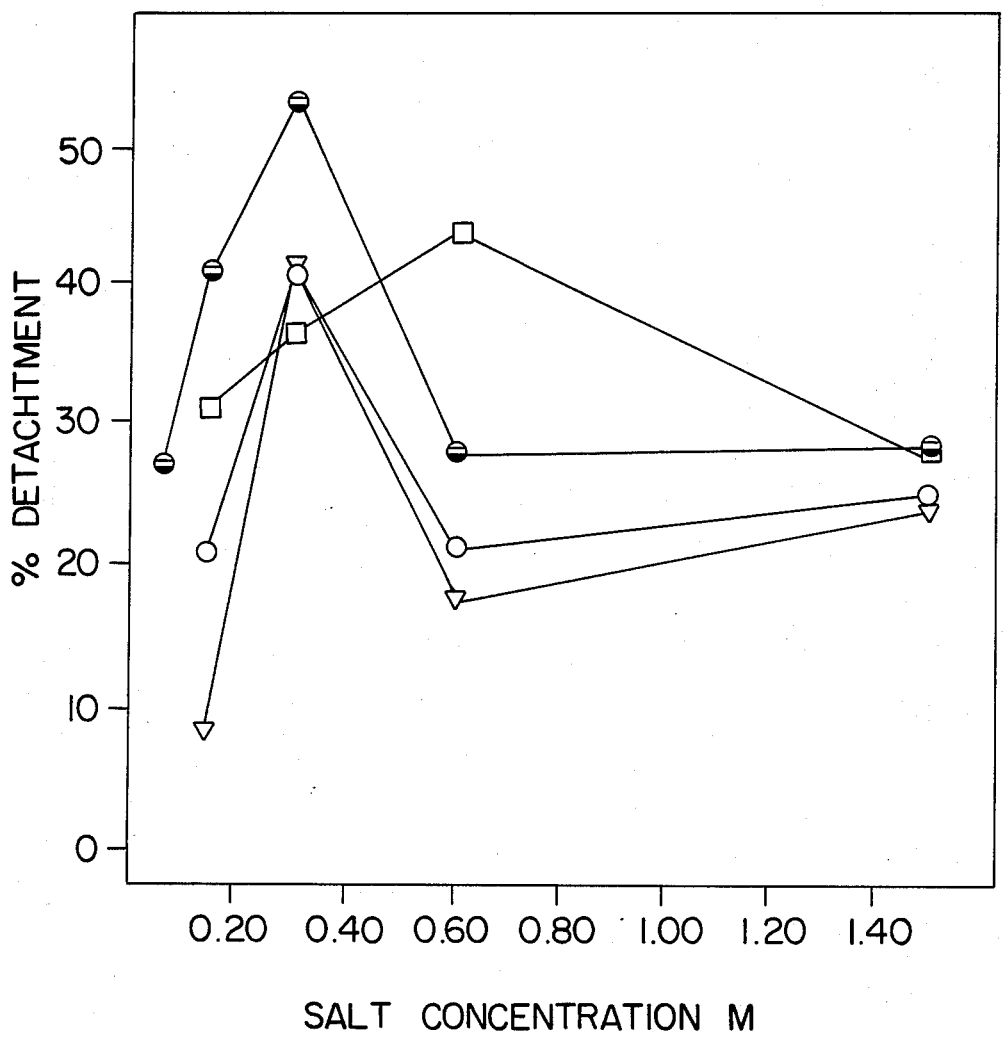
FIG. 1 shows the detachment as a percentage of *Streptococcus mutans* bacteria bound irreversibly to glass, in relation to several salts at various concentrations.

FIG. 1 shows the detachment of irreversibly adhered bacteria after treatment with salt solutions of various concentrations. The salt concentration is expressed in multiples of the basic solution C. The number of irreversibly adhered bacteria was ca. $3.0 \times 10^6$ per glass tube before treatment.

The curves are designated as follows:
● $MgSO_4$  ○ $MgCl_2$  □ $NH_4$Acetate  ▽ $(NH_4)_2SO_4$ The detachment effect can also be seen in the following non-limiting experiments and model systems.

1. A culture of radioactively marked bacteria was attached to hydroxyl apatite beads, either coated or not with parotis saliva (saliva from the salivary gland). The reversibly bound bacteria were then removed by rinsing with a buffer solution so that only irreversibly bound bacteria remained on the hydroxyl apatite beads. These bacteria-coated hydroxyl apatite beads were then exposed to various salt solutions of varying concentration and with the addition of biopolymers. After rinsing, the quantity of bacteria remaining was then determined by measuring the radiation remaining on the hydroxyl apatite beads in a liquid scintillator.

A comparison of the bacteria from the same quantity of hydroxyl apatite which had undergone the same treatment without having been exposed to salt solution or biopolymers enabled assessment of the detachment effect. The result of a number of such detachment experiments on hydroxyl apatite can be found in FIG. 2.

Figure 2:
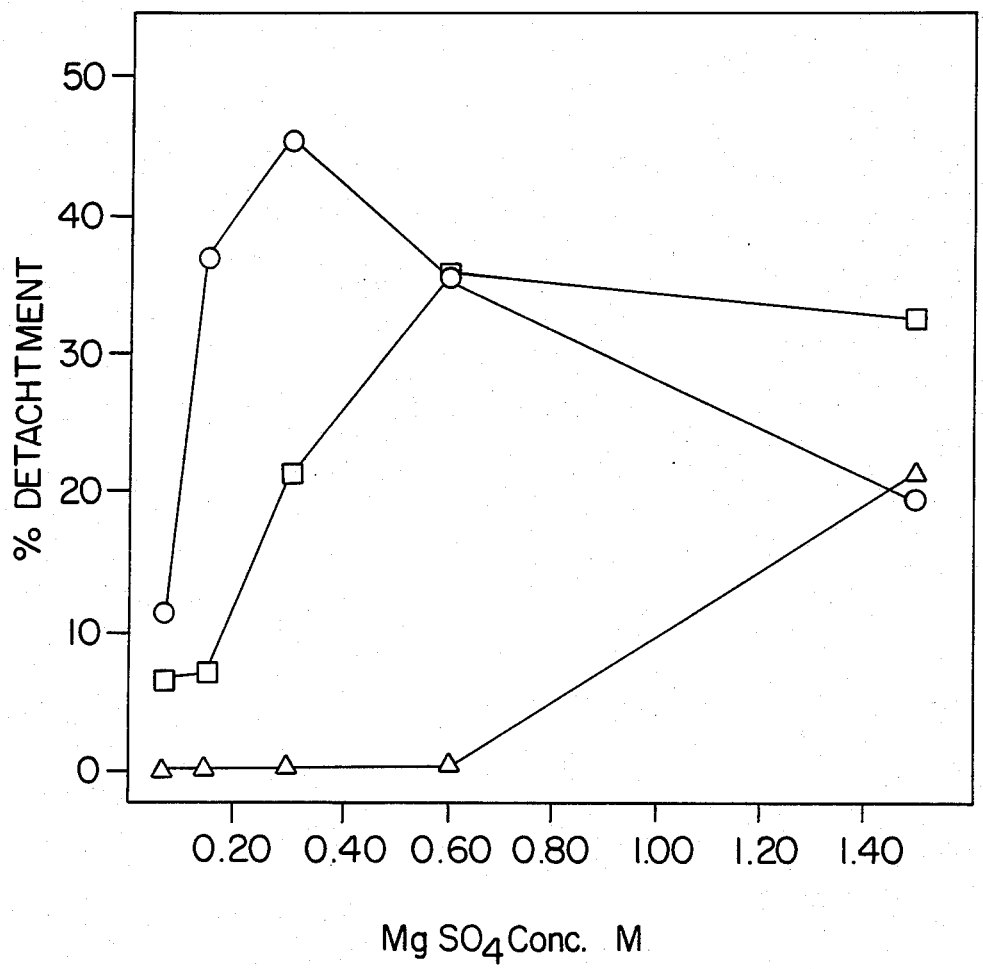
FIG. 2 shows detachment as a percentage of *Streptococcus mutans* bacteria bound irreversibly to hydroxyl apatite, in relation to magnesium sulfate at various concentrations.

The curves in FIG. 2 are designated as follows:
△ hydroxyl apatite beads
○ hydroxyl apatite beads coated in saliva
□ hydroxyl apatite beads coated in saliva and with the addition of 1% aminated starch (CATO 160) to the magnesium sulfate solution.

It can be seen here that the detachment effect of magnesium sulphate on saliva-coated hydroxyl apatite is in the same order of magnitude as described in the example performed earlier. Furthermore, the addition of one (1) biopolymer (aminated starch) has substantially no influence on the maximal detachment.

2. Using the model system with glass tubes described above, further experiments were performed to determine the detachment effect of magnesium sulphate solutions with the addition of biopolymers. The results obtained are shown in FIG. 3.

Figure 3:
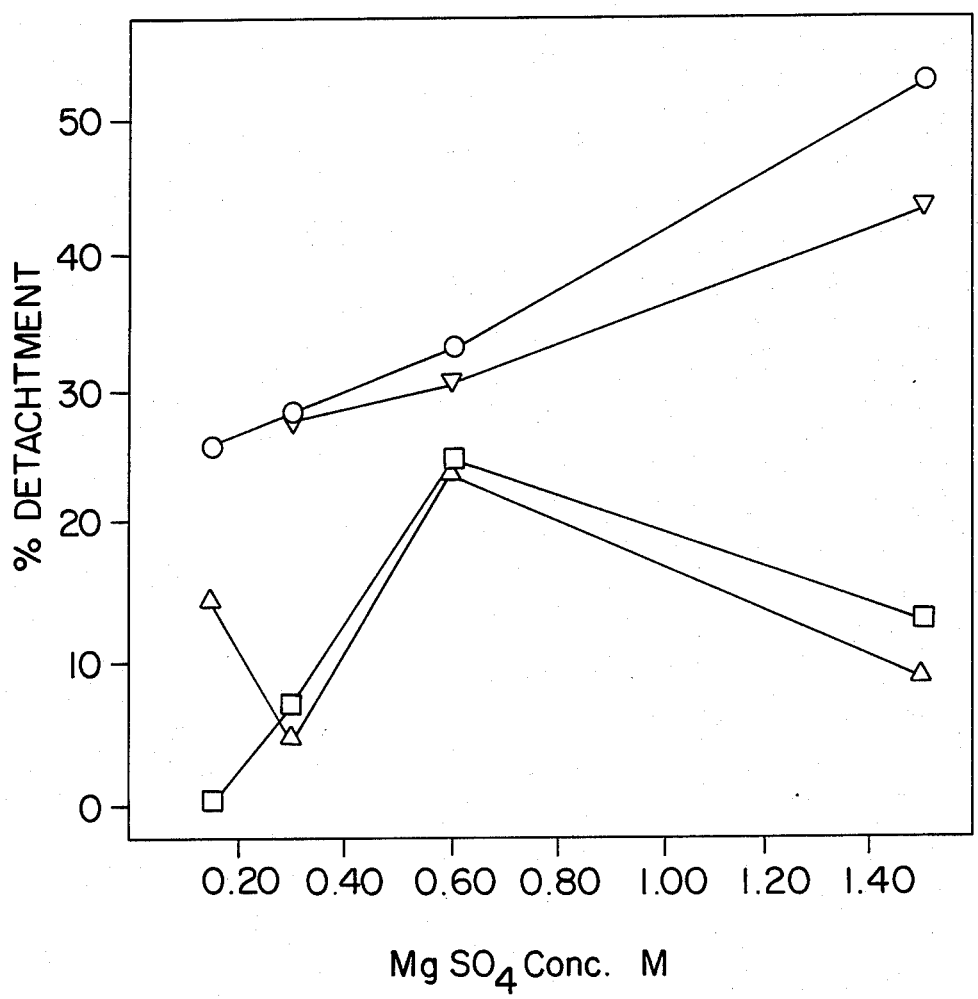
FIG. 3 shows detachment as a percentage of *Streptococcus mutans* bacteria bound irreversibly to glass, in relation to a combination of magnesium sulfate at various concentrations, with various polymers at 1% by weight.

The curves in FIG. 3 are designated as follows:
○ carboxylmethylcellulose 1%
▽ xanthane 1%

☐ aminated starch K 68 1%
△ aminated starch CATO 160 1%

It can be seen here that the detachment effect is not essentially improved by the presence of one (1) of the biopolymers mentioned.

With higher concentrations of magnesium sulphate, the addition of two of the polymers produces a more pronounced detachment effect than with only magnesium sulphate.

Further detachment experiments were carried out using glass tubes as model system. The detachment effect of magnesium sulphate solutions with the addition of two (2) biopolymers to the detachment solution was investigated. Quite surprisingly it was found that several of the biopolymer combinations gave considerably improved detachment effects. The result of these experiments can be seen in FIG. 4. It can be seen here that all the polymer combinations used produce quite a different effect pattern from that obtained previously. It can also be seen that xanthane in combination with other polymers produces a strongly increased detachment effect. The maximum detachment was approximately 90%.

Figure 4:
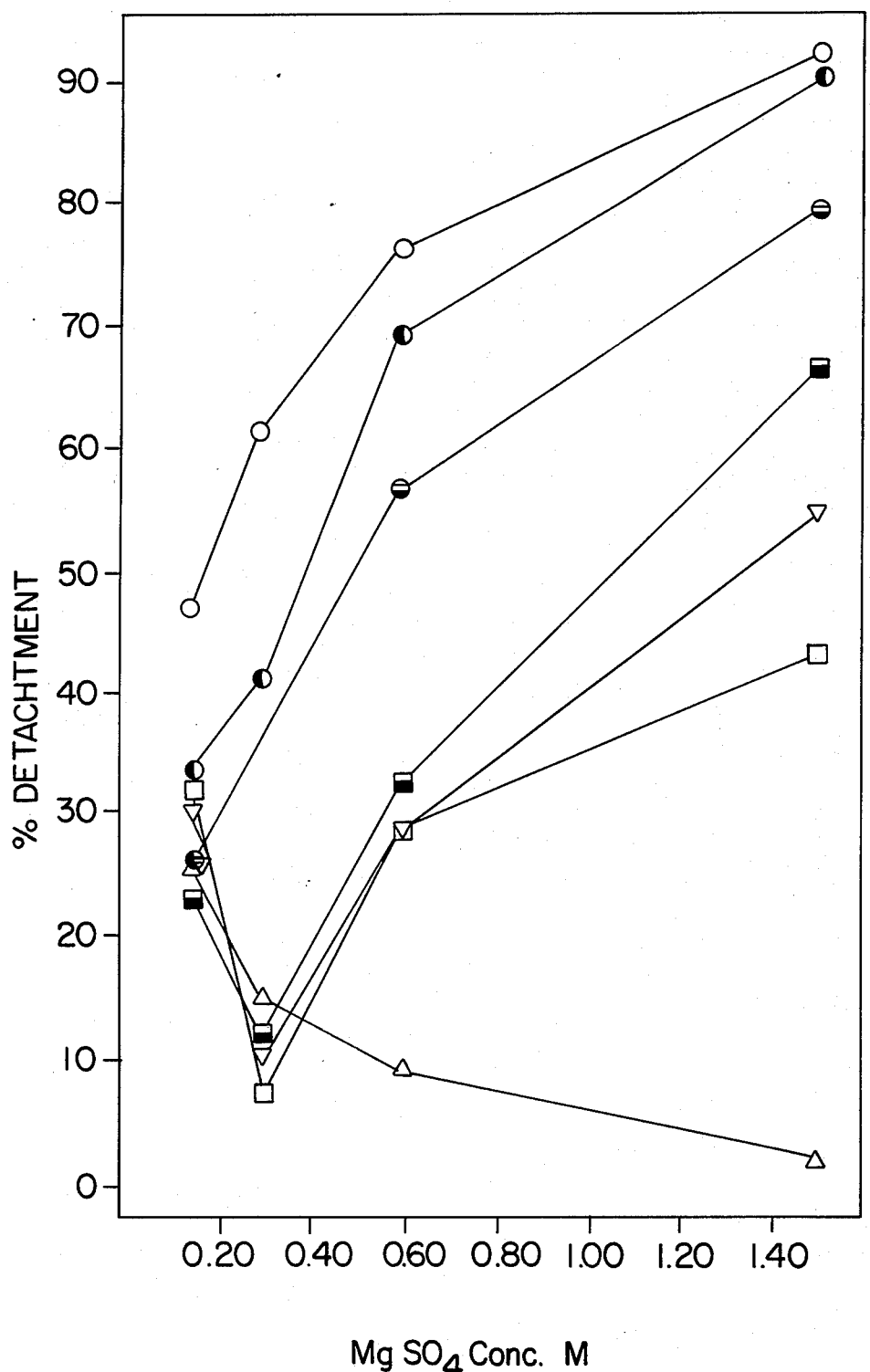
FIG. 4 shows detachment as a percentage of *Streptococcus mutans* bound irreversibly to glass, in relation to magnesium sulfate at various concentrations, together with combinations of two polymers.

The curves in FIG. 4 are designated as follows:
○ xanthane 0.5% and aminated starch K 68 0.5%
◐ xanthane 0.5% and aminated starch CATO 160 0.5%
● xanthane 0.5% and carboxymethylceluose 0.5%
■ carboxymethylcellulose 0.5% and aminated starch
☐ CATO 160 0.5%
▽ aminated starch k 68 0.5% and CATO 160 0.5%
△ cellulose 0.5% and aminated starch K 68 0.5%

The method and preparation of the present invention can be utilized for the removal of micro-organisms from various types of boundary surfaces/inter-phases, e.g. in toothpaste or mouthwashes and in cleansing liquids for wounds.

Besides the biopolymers mentioned above and in conjunction with the figures, other biopolymers and other organic polymers may also be used. The polymers should preferably contain one positively and/or one negativey charged group, e.g. one amino group and/or one carboxyl group.

We claim:

1. A method for increasing detachment of microflora adhered to surfaces and interfaces, comprising administering thereto a solution comprising;
   (a) at least one water soluble organic or inorganic salt selected from the group consisting of lithium, magnesium, aluminum, ammonium, beryllium, and calcium salts, and
   (b) at least two polymer groups selected from the group consisting of positively charged groups, negatively charged groups, amine groups and carboxyl groups.

2. A method according to claim 1, wherein said polymer groups are positively charged groups and negatively charged groups.

3. A method according to claim 1, wherein said polymer groups are amine groups and carboxyl groups.

4. A method according to claim 1, wherein the concentration of said at least one salt is at least about 0.15 molar.

5. A method for increasing detachment of microflora adhered to surfaces and interfaces, comprising administering thereto a solution comprising:
   (a) at least one water soluble organic or inorganic salt selected from the group consising of lithium, magnesium, aluminum, amonium, beryllium, and calcium salts, and
   (b) at least two polymer groups selected from the group consisting of positively charged groups, negatively charged groups, amine groups and carboxyl groups, said polymer groups being supplied by including in said solution at least two polymers selected from the group consisting of xanthan, aminated starch and carboxymethylcellulose.

6. A method according to claim 5, wherein said polymers are xanthane and aminated starch.

7. A method according to claim 5, wherein said polymers are xanthane and carboxymethylcellulose.

8. A method according to claim 5, wherein said polymers are carboxymethylcellulose and aminated starch.

9. A method for increasing detachment of microflora adhered to surfaces and interfaces, comprising administering thereto a solution comprising:
   (a) at least one water soluble organic or inorganic salt selected from the group consisting of lithium, magnesium, aluminum, ammonium, beryllium, and calcium salts, and
   (b) at least two polymer groups selected from the group consisting of positively charged groups, negatively charged groups, amine groups and carboxyl groups, wherein said polymer groups include positively charged groups and negatively charged groups supplied by a single polymer.

10. A composition for increasing detachment of microorganisms adhered to surfaces and interfaces, said composition being a solution consisting essentially of:
    (a) at least one water soluble organic or inorganic salt selected from the group consisting of lithium, magnesium, aluminum, ammonium, beryllium and calcium salts, the concentration of said at least one salt being at least about 0.15 molar,
    (b) at least two polymer groups selected from the group consisting of positively charged groups, negatively charged groups, amine groups and carboxyl groups, and
    (c) water.

11. Composition according to claim 10, wherein said solution contains, as polymer groups, amine groups and carboxyl groups.

12. A composition for increasing detachment of microorganisms adhered to surfaces and interfaces, comprising a solution comprising:
    (a) at least one water soluble organic or inorganic salt selected from the group consisting of lithium, magnesium, aluminum, ammonium, beryllium and calcium salts, the concentration of said at least one salt being at least about 0.15 molar, and
    (b) at least two polymer groups selected from the group consisting of positively charged groups, negatively charged groups, amine groups and carboxyl groups, wherein said polymer groups are supplied by at least two polymers selected from the group consisting of xanthane, aminated starch and carboxylmethylcellulose.

13. Composition according to claim 12, comprising xanthane, together with aminated starch or carboxymethylcellulose.

14. A composition for increasing detachment of microorganisms adhered to surfaces and interfaces, comprising a solution comprising:
    (a) at least one water soluble organic or inorganic salt selected from the group consisting of lithium, aluminum, ammonium, beryllium and calcium salts, the concentration of said at least one salt being at least about 0.5 molar, and (b) at least two polymer groups selected from the group consisting of positively charged groups, negatively charged groups, amine groups and carboxyl groups.

15. A composition according to claim 14, wherein said solution contains as polymer groups, amine groups and carboxyl groups.

* * * * *